US009119973B2

(12) United States Patent
Warr et al.

(10) Patent No.: US 9,119,973 B2
(45) Date of Patent: Sep. 1, 2015

(54) FRAGRANCE COMPOSITION FOR CORE SHELL MICROCAPSULES

(75) Inventors: Jonathan Frank Warr, Paris (FR);
Stuart Bernard Fraser, Neston (GB);
Emmanuel Julien Aussant, Paris (FR)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 12/649,719

(22) Filed: Dec. 30, 2009

(65) Prior Publication Data

US 2010/0168251 A1     Jul. 1, 2010

(30) Foreign Application Priority Data

Dec. 30, 2008  (EP) ..................... 08173121

(51) Int. Cl.
| C11D 3/50 | (2006.01) |
| A61K 8/11 | (2006.01) |
| A61Q 13/00 | (2006.01) |
| A61K 8/34 | (2006.01) |
| A61K 8/35 | (2006.01) |
| A61K 8/37 | (2006.01) |
| A61K 8/49 | (2006.01) |
| A61K 8/60 | (2006.01) |
| C11D 17/00 | (2006.01) |

(52) U.S. Cl.
CPC . *A61Q 13/00* (2013.01); *A61K 8/11* (2013.01);
*A61K 8/34* (2013.01); *A61K 8/347* (2013.01);
*A61K 8/35* (2013.01); *A61K 8/37* (2013.01);
*A61K 8/492* (2013.01); *A61K 8/498* (2013.01);
*A61K 8/60* (2013.01); *C11D 3/505* (2013.01);
*C11D 17/0039* (2013.01); *A61K 2800/412*
(2013.01)

(58) Field of Classification Search
CPC ......... A61Q 19/00; A61Q 15/00; A61Q 5/02;
A61Q 13/00; A61Q 19/10; A61Q 5/12;
A61Q 17/04; C11D 17/0039; C11D 3/505;
C11D 11/02; C11D 17/0013; C11D 17/0047;
C11D 3/001
USPC ............... 428/402, 402.24; 264/4, 4.33, 4.32;
427/212, 213, 213.3, 213.31, 483;
512/1, 4; 239/53; 424/601, 610, 611;
525/902; 510/523, 520, 528, 191, 515,
510/101, 102, 220, 524, 505, 437, 516, 238,
510/322, 527, 522, 441, 267, 475, 130;
523/201; 514/772, 773, 252, 774
See application file for complete search history.

(56) References Cited

U.S. PATENT DOCUMENTS

| 2,800,457 | A |  | 7/1957 | Green et al. |
| 3,415,758 | A |  | 12/1968 | Powell et al. |
| 5,585,343 | A |  | 12/1996 | McGee et al. |
| 6,103,678 | A | * | 8/2000 | Masschelein et al. ........ 510/101 |
| 6,110,449 | A |  | 8/2000 | Bacon et al. |
| 6,261,483 | B1 |  | 7/2001 | Frank et al. |
| 6,696,395 | B1 | * | 2/2004 | Woo et al. ...................... 510/101 |
| 2002/0055452 | A1 |  | 5/2002 | McGee et al. |
| 2003/0228992 | A1 | * | 12/2003 | Smets et al. .................. 510/267 |
| 2004/0220064 | A1 | * | 11/2004 | McGee et al. ................ 510/130 |
| 2005/0112152 | A1 |  | 5/2005 | Popplewell et al. |
| 2005/0227907 | A1 | * | 10/2005 | Lee et al. .......................... 512/4 |
| 2006/0154850 | A1 | * | 7/2006 | Quellet et al. .................... 512/2 |
| 2007/0082829 | A1 |  | 4/2007 | Smets et al. |
| 2007/0135319 | A1 |  | 6/2007 | Wei et al. |

FOREIGN PATENT DOCUMENTS

| EP |  | 0466235 |  | * | 1/1992 | ............... C11D 3/50 |
| EP |  | 0659876 | A2 | * | 6/1995 | ............... C11D 3/39 |
| EP |  | 1502646 | A1 |  | 2/2005 |  |
| EP |  | 1589092 | A1 |  | 10/2005 |  |
| EP |  | 1767185 | A1 | * | 3/2007 | ............... A61K 8/11 |
| JP |  | 61-260860 | A |  | 11/1986 |  |
| JP |  | 11-139923 | A |  | 5/1999 |  |
| JP |  | 2006-511322 | A |  | 4/2006 |  |
| JP |  | 2007-092067 | A |  | 4/2007 |  |
| JP |  | 2007092067 | A | * | 4/2007 | ................ C11B 9/00 |
| JP |  | 2008-063575 | A |  | 3/2008 |  |
| JP |  | 2008-063675 | A |  | 3/2008 |  |
| WO |  | 00/59616 | A1 |  | 10/2000 |  |
| WO | WO | 2004/098667 |  | * | 11/2004 | ............. A61L 15/46 |
| WO |  | 2006/097427 | A1 |  | 9/2006 |  |
| WO |  | 2007/052224 | A2 |  | 5/2007 |  |

(Continued)

OTHER PUBLICATIONS

Peonil The Good Scents Company {http://www.thegoodscentscompany.com/data/rw1131081.html} with CAS data Cyclohexylphenylacetonitrile {http:www.chemnet.com/cas/en/3893-23-0/Cyclohexylphenylacetonitrile.html} and Chemsynthesis structure: 2-cyclohexyl-2-phenylacetonitrile {http://www.chemsynthesis.com/base/chemical-structure-14028.html}.*

(Continued)

*Primary Examiner* — James J Seidleck
*Assistant Examiner* — S. Camilla Pourbohloul
(74) *Attorney, Agent, or Firm* — Sughrue Mion, PLLC

(57) ABSTRACT

The invention relates to a core shell microcapsules containing a fragrance composition which comprises, prior to encapsulation: A) 40 to 100% by weight of at least one cyclic aromachemical material with a density between 0.950 g/cm$^3$ and 1.500 g/cm$^3$ and a ClogP value between 1.00 and 6.00; B) 0 to 80% by weight of at least one fragrance material with a density between 0.630 g/cm$^3$ and 0.950 g/cm$^3$; and C) 0 to 50% by weight of at least one oil soluble organic compound having a density between 0.950 g/cm$^3$ and 1.500 g/cm$^3$, where the sum of A), B) and C) equals 100%.

12 Claims, No Drawings

(56) References Cited

FOREIGN PATENT DOCUMENTS

| WO | 2007/130684 A1 | 11/2007 | | |
|---|---|---|---|---|
| WO | 2008/098387 A1 | 8/2008 | | |
| WO | WO2008098387 | * | 8/2008 | ............... A61K 8/11 |

OTHER PUBLICATIONS

Benzyl Salicylate The Good Scents Company {http://www.thegoodscentscompany.com/data/rw1001791.html}.*
Diethyl phthalate The Good Scents Company {http://www.thegoodscentscompany.com/data/rw1004351.html}.*
Hexyl Salicylate The Good Scents Company {http://www.thegoodscentscompany.com/data/rw1002751.html}.*
Hexyl Cinnamic Aldehyde The Good Scents Company {http://www.thegoodscentscompany.com/data/rw1005971.html}.*
ISO Super E The Good Scents Company {http://www.thegoodscentscompany.com/data/rw1020611.html}.*
Hedione The Good Scents Company {http://www.thegoodscentscompany.com/data/rw1015271.html}.*
Cyclamen aldehyde The Good Scents Company {http://www.thegoodscentscompany.com/data/rw1004111.html}.*
Anisic aldehyde The Good Scents Company {http://www.thegoodscentscompany.com/data/rw1001271.html}.*
Lilial The Good Scents Company {http://www.thegoodscentscompany.com/data/rw1008611.html}.*
d-limonene The Good Scents Company {http://www.thegoodscentscompany.com/data/rw1013771.html}.*
Citronellol The Good Scents Company {http://www.thegoodscentscompany.com/data/rw1007031.html}.*
Tide Brand MSDS P and G Jan. 29, 2003 PGC41674.pdf.*
Frideli et al Proceedings of the World Conference on Lauric oils Sources Processing and Applications 1994 pp. 133-137.pdf.*
Acetyl tributyl citrate MSDS ABEL Jun. 1 2006 77-90-7_Abel.pdf.*
Product Data sheet diethyl phthalate printed Nov. 12, 2011 {http://thegoodscentscompany.com/data/rw1004351.html}.*
Triacetin MSDS Science Lab {creation date Oct. 10, 2005 printed Nov. 12, 2011) {http://www.sciencelab.com/msds.php?msdsId=9925295}.*
Extended Search Report dated Aug. 12, 2009 issued by the European Patent Office in counterpart application No. 08173121.8.
Japanese Patent Office, Third Party Submission dated Feb. 22, 2011, in corresponding Application No. 2009-297038.
Japan Patent Office, Office Action dated May 27, 2014 issued in Japanese Application No. 2009-297038.

* cited by examiner

FRAGRANCE COMPOSITION FOR CORE SHELL MICROCAPSULES

CROSS-REFERENCE TO RELATED APPLICATIONS

This application claims priority from European Patent Application No. 08 173 121.8 filed on Dec. 30, 2008, the entire subject matter of which is incorporated herein by reference.

BACKGROUND OF THE INVENTION

1. Technical Field of Invention

The invention relates to fragrance compositions to be incorporated into the core of core shell type microcapsules to control the delivery and release of fragrance and optionally other benefit agents, when used as components within liquid household, laundry, personal care and cosmetic products.

The invention further relates to the use of these microcapsules in liquid consumer products, especially household cleaners, laundry products, and personal care, and cosmetic products including thickened and shear thinning liquids which may appear to be gels under conditions of low shear.

2. Background of the Invention

It is known to encapsulate water insoluble fragrances or other non-fragrance materials in small capsules, often termed microcapsules, typically having a diameter between 1 and 1000 micrometers (microns), for a variety of reasons relating to the protection, delivery and release of the fragrance or other materials.

The preparation of microcapsules is described in Kirk Othmer's Encyclopaedia of Chemical Technology 5th edition and also in the following patents U.S. Pat. No. 2,800,457, U.S. Pat. No. 3,415,758 and U.S. Pat. No. 6,261,483 and references therein. One type of microcapsules, referred to as a wall or shell or core shell microcapsule, comprises a generally spherical shell of water- and oil-insoluble materials, typically a network polymer material, within which fragrance or other material is contained.

When such capsules are incorporated in liquid consumer products, e.g. personal care products such as shampoos, hair conditioners, body washes, or shower gels, laundry products such as fabric conditioners or liquid laundry detergents, or household cleaners such as kitchen surface cleaners, problems can arise, with the microcapsules either creaming (rising to the surface) or settling over time, especially if the product is stored. The creaming or settling is due to differences in density between the microcapsule, its contents and the surrounding liquid. Many liquid household cleaners, liquid laundry products and personal care and cosmetic products have densities around 1.00 g per cubic centimeter ($g/cm^3$), while many organic compounds have densities lower than 1.00 $g/cm^3$. So a microcapsule containing a high proportion of fragrance oils or other hydrophobic oils may have a lower density than the liquid phase of the product in which the microcapsules are dispersed, hence these microcapsules will tend to rise or cream over time.

From known physical laws it is possible to calculate a theoretical maximum size for a capsule to remain stably dispersed within a liquid.

Below is an equation for the rate of creaming/settling of an emulsion derived from Stokes law:

$$v = \frac{2a^2(d_o - d)g}{9\eta}$$

v=velocity of creaming/settling;
a=the particle radius;
$d_o$=the density of the continuous phase;
d=the density of the dispersed phase (microcapsule);
g=the gravitational constant;
$\eta$=the viscosity of the continuous phase assuming Newtonian shear.

It should be noted that this equation assumes the particles are spherical, uniform and not flocculated. More complex equations but essentially of the same form can be derived for particles of mixed sizes. Also this equation does not include any effects due to Brownian motion which will keep a very small particle dispersed. Despite describing an ideal model and thus not exact for real samples the equation sets out the important factors which govern particle creaming or settling.

It may not be possible or desirable to prepare microcapsules of different (usually smaller) size to reduce creaming or settling as this may have other consequences, such as affecting the ease of breaking the walls for those microcapsules which rely on friability for content release. Moreover less material is encapsulated into a smaller microcapsule requiring a higher proportion of wall material relative to content and a larger number of microcapsules to contain the same amount of core material which consequently may affect product attributes such as colour and importantly cost of manufacture. It may also be undesirable to increase the viscosity of the liquid product in which the microcapsules are dispersed hence it is preferred if the densities of the microcapsules and liquid phase can be more equally balanced.

US patent application 2005/112,152 describes adding solvents to core shell encapsulated fragrances but stipulates that the fragrances must have ClogP greater than 3.3, preferably greater than 8. It is clear from the context that density was not a consideration in selecting these materials since the majority of those named fragrances have densities lower than 1.0 $g/cm^3$ and the higher ClogP requirements suggest that larger alkyl groups are preferred such as glyceryl tributyrate rather than glyceryl triacetate although the latter would be preferred as a density raising ingredient.

EP patent application 1502646 describes density modifiers for co-acervate microcapsules for detergent liquid products but only describes materials which lower the density of the microcapsule.

International application WO 00/59616 also describes modifying the microcapsule contents in order to balance the density with the surrounding liquid. However the materials suggested for raising the density are not very suitable for personal care, laundry and household products being some high density salts or high density hydrophobic liquids such as those containing halogens. It is not desirable or in many cases permissible to include halogenated organic compounds into microcapsules intended for domestic consumer products since many such compounds are believed to have adverse effects on the environment and/or on health.

Surprisingly few organic compounds have densities greater than 0.950 $g/cm^3$ even fewer have densities greater than 1.00 $g/cm^3$ especially if all organic compounds containing halogen atoms are excluded. Compounds having higher densities tend to comprise a substantial proportion of oxygen, nitrogen and sulphur atoms in their molecular formulae and/or possess rings such as aromatic rings in their chemical structures. However such compounds are often quite hydrophilic owing to the polar nature of many functional groups containing oxygen, nitrogen or sulphur atoms. Consequently such hydrophilic compounds may not be efficiently encapsulated by emulsion polymerization techniques.

A further requirement is that encapsulated molecules should not leak from the microcapsules during storage and it has been observed that small molecules and/or more water soluble molecules leak quite quickly, especially from microcapsules made by amine and aldehyde condensation reactions.

So whilst it is advantageous if the densities of microcapsules can be closely balanced to the density of the liquid product into which they are to be dispersed, this is particularly difficult to achieve for liquid products having densities greater than 1.010 g/cm$^3$. Furthermore from the diverse constraints on the properties of microcapsule core materials and the need that the fragrance must be of sufficient quality to be acceptable in a premium commercial product, it is not immediately apparent that the density of the fragrance composition for a core shell microcapsule can be controlled to be close to or even greater than 0.950 g/cm$^3$ just by formulating the contents from high density fragrance compounds.

SUMMARY OF THE INVENTION

The present invention encompasses the following embodiments.

(1) A core shell microcapsule which has an average particle size between 1 and 500 micrometers and contains a fragrance composition which comprises, prior to encapsulation:

A) 40 to 100% by weight of at least one cyclic aromachemical material with a density between 0.950 g/cm$^3$ and 1.500 g/cm$^3$ and a ClogP value between 1.00 and 6.00;

B) 0 to 80% by weight of at least one fragrance material with a density between 0.630 g/cm$^3$ and 0.950 g/cm$^3$; and C) 0 to 50% by weight of at least one oil soluble organic compound having a density between 0.950 g/cm$^3$ and 1.500 g/cm$^3$, where the sum of A), B) and C) equals 100%.

(2) The core shell microcapsule according to (1), wherein the fragrance composition comprises between 40% and 100% by weight of the cyclic aromachemical material A) with a density between 1.000 g/cm$^3$ and 1.500 g/cm$^3$ and a ClogP value between 1.50 and 5.00.

(3) The core shell microcapsule according to (1) or (2), wherein the fragrance composition comprises between 75% and 100% by weight of the cyclic aromachemical material A) having a ClogP value between 2.00 and 4.50.

(4) The core shell microcapsule according to any one of (1) to (3), wherein the fragrance composition comprises between 5 and 60% by weight of the at least one fragrance material B) with a density between 0.630 g/cm$^3$ and 0.950 g/cm$^3$.

(5) The core shell microcapsule according to any one of (1) to (4), wherein the cyclic aromachemical material A) and fragrance material B) comprise at least 10 kinds of fragrance materials in total.

(6) The core shell microcapsule according to any one of (1) to (5), wherein the fragrance composition comprises between 10 and 50% by weight of the at least one oil soluble organic compound C) having a density between 0.950 g/cm$^3$ and 1.500 g/cm$^3$.

(7) The core shell microcapsule according to any one of (1) to (6), wherein the cyclic aromachemical material A) is selected among benzyl acetate, benzophenone, benzyl salicylate, c is 3-hexenyl salicylate, coumarin, cyclohexyl salicylate, 3a,4,5,6,7,7a-hexahydro-4,7-methano-1H-inden-5(or 6)-yl acetate, ethylvanillin, eugenol, heliotropine, indole, isoeugenol, methyl anthranilate, methyl benzoate, oxane (2-methyl-4-propyl-1,3-oxathiane), 2-phenylethanol, vanillin, vanillin isobutyrate and watermelon ketone and mixtures thereof.

(8) The core shell microcapsule according to any one of (1) to (7), wherein the fragrance material B) is selected among allyl caproate, citronellol, gamma decalactone, dihydromyrcenol, cis-3-hexenyl acetate, limonene, linalool, prenyl acetate and butyl cyclohexyl acetate and mixtures thereof.

(9) The core shell microcapsule according to any one of (1) to (8), wherein the oil soluble organic compound C) is selected among acetyl triethyl citrate, diethyl maleate, diethyl malonate, diethyl adipate, dimethyl adipate, diethyl succinate, diethyl tartarate, dimethyl terephthalate, glyceryl triacetate, propylene glycol diacetate, sucrose octa-acetate, sucrose diacetate hexaisobutyrate, glyceryl tripropionate, triethyl citrate and mixtures thereof.

(10) The core shell microcapsule according to any one of (1) to (9), wherein the fragrance composition further comprises:

D) 0 to 50% by weight of at least one solvent with a density below 0.950 g/cm$^3$, where the sum of A), B), C) and D) equals 100%, and where the sum of C) and D) is 50% by weight or less.

(11) The core shell microcapsule according to any one of (1) to (10), wherein the fragrance composition has a density greater than 0.950 g/cm$^3$.

(12) A liquid consumer product having a density greater than 1.010 g/cm$^3$ and a viscosity between 10 mPas and 5000 mPas measured at either 25° C. or 40° C., which contains the core shell microcapsule as defined in any one of (1) to (11).

(13) The liquid consumer product according to (12), having a viscosity between 10 mPas and 2500 mPas measured at either 25° C. or 40° C.

(14) The liquid consumer product according to (12) or (13), which is a household, laundry, personal care or cosmetic composition, and which comprises at least 2% by weight a surfactant.

(15) The liquid consumer product according to (14), in which water is the largest component by weight percent.

Illustrative aspects of the present invention provide a fragrance composition for a core shell microcapsule which comprises:

A) 20 to 100% by weight of at least one cyclic aromachemical material with a density between 0.950 g/cm$^3$ and 1.500 g/cm$^3$ and a ClogP value between 1.00 and 6.00;

B) 0 to 80% by weight of at least one fragrance material with a density between 0.630 g/cm$^3$ and 0.950 g/cm$^3$; and C) 0 to 50% by weight of at least one oil soluble organic compound having a density between 0.950 g/cm$^3$ and 1.500 g/cm$^3$;

where the sum of A), B) and C) equals 100%.

Preferred fragrance compositions are those which comprise between 30% and 100% by weight of cyclic aromachemical materials with densities between 0.950 g/cm$^3$ and 1.500 g/cm$^3$, preferably between 1.000 g/cm$^3$ and 1.500 g/cm$^3$, more preferably between 1.050 g/cm$^3$ and 1.400 g/cm$^3$ and ClogP values between 1.50 and 5.00 and even more preferably between 2.00 and 4.50.

Preferred fragrance compositions also include those which comprise between 35% and 100% by weight of cyclic aromachemical materials with densities between 0.950 g/cm$^3$ and 1.500 g/cm$^3$, preferably between 1.000 g/cm$^3$ and 1.500 g/cm$^3$, more preferably between 1.050 g/cm$^3$ and 1.400 g/cm$^3$ and ClogP values between 1.50 and 5.00 and even more preferably between 2.00 and 4.50.

More preferred fragrance compositions are those which comprise between 40% and 100% by weight of cyclic aromachemical materials with densities between 0.950 g/cm³ and 1.500 g/cm³, preferably between 1.000 g/cm³ and 1.500 g/cm³, more preferably between 1.050 g/cm³ and 1.400 g/cm³ and ClogP values between 1.50 and 5.00 and even more preferably between 2.00 and 4.50.

Even more preferred compositions are those which comprise between 50% and 100% by weight of cyclic aromachemical materials with densities between 0.950 g/cm³ and 1.500 g/cm³, preferably between 1.000 g/cm³ and 1.500 g/cm³, more preferably between 1.050 g/cm³ and 1.400 g/cm³ and ClogP values between 1.50 and 5.00 and even more preferably between 2.00 and 4.50.

Especially preferred compositions are those which comprise between 60% and 100% by weight of cyclic aromachemical materials with densities between 0.950 g/cm³ and 1.500 g/cm³, preferably between 1.000 g/cm³ and 1.500 g/cm³, more preferably between 1.050 g/cm³ and 1.400 g/cm³ and ClogP values between 1.50 and 5.00 and even more preferably between 2.00 and 4.50.

More especially preferred fragrance compositions are those which comprise between 75% and 100% by weight of cyclic aromachemical materials with densities between 0.950 g/cm³ and 1.500 g/cm³, preferably between 1.000 g/cm³ and 1.500 g/cm³, more preferably between 1.050 g/cm³ and 1.400 g/cm³ and ClogP values between 1.50 and 5.00 and even more preferably between 2.00 and 4.50.

In one aspect of the invention it is preferred if the core shell microcapsule is formed predominantly by the condensation of aldehydes and amines or urea. Predominantly means more than 50% by weight of the capsule wall. The remainder of the capsule wall may comprise other polymers such as polyurethanes or gelatin or carageenan or free radical addition polymers from vinylic or acrylic monomers such as polyacrylamides, or polyacrylate esters polyvinyl acetates or copolymers of any of these.

The encapsulated fragrance composition of the invention is suitable for use in liquid surfactant-containing consumer products which have a density greater than 1.010 g/cm³ at 20° C. and having a viscosity between 10 mPas and 5,000 mPas, preferably between 10 mPas and 2,500 mPas measured at either 25° C. or 40° C., preferably a viscosity between 10 mPas and 5,000 mPas, preferably between 10 mPas and 2,500 mPas measured at 25° C.

DETAILED DESCRIPTION OF THE INVENTION

In this specification, all percentages quoted are weight percent unless otherwise stated. Percentages which refer to fragrance compositions are based on the composition prior to emulsification and encapsulation and not to the encapsulated fragrance composition. All documents cited in this specification are incorporated herein by reference.

The density of a substance is defined as the quotient of its mass and volume and is expressed in grams per cubic centimeter (g/cm³). Several methods are available for determining the density of substances; the most common ones are described in the OECD Guideline for the Testing of Chemicals No 109 adopted by the Council on 27, Jul. 1995. ASTM D4052 describes the procedure for measuring densities of liquids with a digital density meter using the oscillating U-tube principle.

The densities of liquid mixtures mentioned in the present specification have been measured using a Mettler Toledo DR40 digital density meter at 20° C. following the procedure of ASTM D4052, unless otherwise stated. Densities of liquid ingredients are measured in the same way or values are taken from the published literature e.g. from the 2008-2009 chemical catalogue of the Sigma Aldrich company or Beilstein database (2008/02) from Elsevier Information Systems GmbH as secondary data sources. Densities for solid materials with melting points above 35° C. are measured as liquids at the temperatures stated or are taken from the literature and referenced.

Density is a ratio of two measured values and so subject to bias and variation depending on the methods and test conditions used. Reproducibility with a digital density meter is less than 0.001 g/cm³ and bias also less than 0.001 g/cm³ compared with a pycnometer method. Thus for the purposes of the present specification densities are only quoted to three decimal places and the fourth decimal place is rounded up or down according to the usual convention. In case of disputed values for liquid samples at ambient temperature, the digital density meter is the designated method for density determination as described in ASTM D4052.

In the present specification, the term "high density" is used for densities greater than 0.950 g/cm³ at 20° C.

Viscosities are measured at 25° C., using a Brookfield LVT viscometer with spindle No. 31 at 30 rpm unless otherwise stated.

For the purpose of the present specification the term "organic compound" means a chemical compound containing only atoms from among, but not necessarily containing all of, the following: carbon, hydrogen, oxygen, sulphur and nitrogen. A high density organic compound is a compound consisting of atoms from among the group carbon, hydrogen, oxygen, sulphur and nitrogen, having a density greater than 0.950 g/cm³ preferably greater than 1.000 cm³ and even more preferably greater than 1.050 g/cm³.

The term "cyclic" or the word "ring" in the context of molecular structure in the present specification refers to a series of atoms which form a closed ring within a molecule e.g. cyclohexane rather than the open chain aliphatic compound hexane. Aromatic rings are those capable of undergoing electrophilic substitution reactions rather than the addition reactions which occur with non aromatic unsaturated compounds. They can also be defined as planar rings having $(4n+2)\pi$ electrons according to Hückels rule and include arenes and heteroarenes. The term cyclic also includes heterocyclic rings and substituted ring molecules. Further definitions of chemical nomenclature as used in this text can be found in "G. P. Moss, P. A. S. Smith and D. Tavernier, Pure and Applied Chemistry, vol. 67 pp 1307-1375 1995."

Fragrance Materials

In the context of this specification the term fragrance composition is understood to be synonymous with the terms "perfume composition" or "perfume" and to refer to a mixture of olfactively active materials providing a pleasant smell. The term fragrance ingredient which is also synonymous with the terms "fragrance component", "perfume ingredient" and "perfume component" is taken to mean any individual material which may be an ingredient within the fragrance composition even though that fragrance ingredient may itself comprise many individual chemical compounds and possess a pleasant smell. This distinction is understood by those familiar with the art of fragrance creation.

A wide variety of odiferous materials are known for perfumery use, including materials such as alkenes, alcohols, aldehydes, ketones, esters, ethers, nitriles, amines, oximes, acetals, ketals, thiols, thioketones, imines, etc. Without wishing to be limited, the fragrance ingredients of the core composition will preferably have molecular weights of less than 325 atomic mass units, preferably less than 300 mass units and more preferably less than 275 atomic mass units to ensure sufficient volatility to be noticeable when the microcapsules release. Furthermore the fragrance ingredients will preferably have molecular weights greater than 75 atomic mass units, preferably greater than 100 atomic mass units, more preferably greater than 150 atomic mass units as lower masses may be too volatile to be effective as part of a fragrance, or too water soluble to be emulsified during encapsulation. Ingredients of the fragrance compositions will not contain strongly ionizing functional groups such as sulphonates, sulphates, or quaternary ammonium ions, nor will they contain any halogen atoms. Indeed fragrance ingredients of the invention will be comprised of compounds containing only atoms from among, but not necessarily all of, the following: hydrogen, carbon, oxygen, nitrogen and sulphur.

Fragrance ingredients and fragrance solvents are described more fully in S. Arctander, Perfume Flavors and Chemicals. Vols. I and II, Montclair, N.J. and in Allured's Flavor and Fragrance Materials 2007 ISBN 978-1-93263326-9 published by Allured Publishing Corp.

Preferably fragrance ingredients which are suitable for inclusion in the core of a core shell microcapsule are unaffected by the chemical reactions of the encapsulation process.

Naturally occurring plant oils and exudates comprising complex mixtures of various chemical components are also known for use as fragrances, and such materials can be used herein although each material is considered as a single ingredient despite it being well known that most natural extracts are mixtures of compounds. The principal chemical components of most relevant natural materials are known, thus for the most part they can be assessed in the same way as synthetic aroma chemicals.

Fragrance Solvents

It is common to use solvents within fragrances either as liquid solubilising agents for solid fragrance ingredients or as diluents for the more potent ingredients or to control the vapour pressure and evaporation characteristics of the fragrance. Solvents may have many of the characteristics of fragrance ingredients but they do not have strong odours in themselves. Indeed solvents may be distinguished from fragrance ingredients because they can be added to fragrance compositions in high proportions such as 30% or even 50% by weight without significantly changing the odour quality of the fragrance composition. Solvents are to be treated as belonging to category Ciii) or D. Some examples of fragrance solvents include acetyl triethylcitrate, benzyl benzoate, dipropylene glycol, diethylphthalate, isopropyl myristate, propylene glycol, and triethyl citrate.

Oil Soluble Benefit Agents

Benefit agents are defined as non fragrance materials which may be incorporated into capsule cores to provide benefits other than fragrance when capsules are ruptured and the contents released. Oil soluble in the context of the present specification means materials which have a solubility greater than 1.5 g per 100 g of diethyl phthalate at 20° C. after 48 hours. Typical benefit agents include sunscreen compounds, insect repellants, pro-fragrances and materials which provide a warming or cooling effect such as described in Cosmetics and Toiletries Vol. 120 No 5 p. 105 by M Erman and materials which suppress or reduce malodour and its perception by any of the many mechanisms proposed. Materials which improve the properties of the core emulsion before encapsulation, or the properties of the capsules themselves are also benefit agents. Sometimes fragrance materials may have secondary functions and confer another benefit on a composition e.g. salicylate esters may act as sunscreen agents as well as fragrance molecules. Benefit agents which are also fragrance ingredients will be classified as fragrance ingredients i.e. belonging to either of categories A or B otherwise benefit agents are treated as fragrance solvents.

In order that the encapsulated fragrance should give a noticeable fragrance on release and be appreciated as a high quality fragrance appropriate for a premium consumer product, a fragrance composition for encapsulation should preferably contain at least 4 kinds of fragrance ingredients, more preferably at least 10 kinds of fragrance ingredients and even more preferably at least 15 kinds of fragrance ingredients which can comprise a mixture of natural and synthetic ingredients chosen to create any desired odour. Additionally, it is preferable that no single chemical compound should comprise more than 70% by weight of the total fragrance composition, more preferably that no single chemical compound comprises more than 60% by weight of the total fragrance composition and even more preferably that no single chemical compound comprises more than 50% by weight of the total fragrance composition.

ClogP refers to the octanol/water partitioning coefficient (P) of fragrance ingredients. The octanol/water partitioning coefficient of a fragrance ingredient is the ratio between its equilibrium concentrations in octanol and in water. The partitioning coefficients of fragrance ingredients are more conveniently given in the form of their logarithm to the base 10, logP. Thus the fragrance ingredients of this invention have logP of about 1.00 to 6.00, preferably in the range 1.50 to 5.00 and more preferably in the range 2.00 to 4.50. The logP values of many fragrance ingredients have been reported; for example, the Pomona92 database, available from Daylight Chemical Information Systems, Inc. (Daylight CIS), Irvine, Calif., contains many, along with citations to the original literature. However, the ClogP values reported herein are most conveniently calculated by the "CLOGP" program available within the Chemoffice Ultra Software version 9 available from CambridgeSoft Corporation, 100 CambridgePark Drive, Cambridge, Mass. 02140 USA or CambridgeSoft Corporation, 8 Signet Court, Swanns Road, Cambridge CBS 8LA UK. The ClogP values are preferably used instead of the experimental logP values in the selection of fragrance ingredients which are useful in the present invention. For natural oils or extracts the composition of such oils can be determined by analysis or using the compositions published in the ESO 2000 database published by BACIS (Boelens Aroma Chemical Information Service, Groen van Prinsterlaan 21, 1272 GB Huizen, The Netherlands).

It is preferable that the fragrance composition is sufficiently insoluble in water to form an emulsion as part of the encapsulation process. Since water solubility is approximately inversely correlated with ClogP it is preferable that more than 50% by weight, preferably more than 70% by weight, of the fragrance composition comprises cyclic aromachemical materials having ClogP values between 1.00 and 6.00, more preferable is that more than 50% by weight and more preferably more than 70% by weight have ClogP values between 1.50 and 5.00 and even more preferable is that more than 50% by weight and preferably more than 70% by weight have ClogP values between 2.00 and 4.50.

The fragrance composition preferably has a density greater than 0.950 g/cm$^3$.

High Density Cyclic Aromachemical Materials (Category A)

An essential feature of the invention is that 20% to 100% of the fragrance composition for encapsulation should contain at least one cyclic aromachemical material with a density between 0.950 g/cm$^3$ and 1.500 g/cm$^3$. Preferably, the fragrance composition comprises 20 to 100% of at least 3 kinds of and more preferably at least 6 kinds of and especially preferably at least 10 kinds of high density cyclic aromachemical materials with a density between 0.950 g/cm$^3$ and 1.500 g/cm$^3$. Suitable high density cyclic aromachemical materials are defined as fragrance ingredients which contain at least one ring in the chemical structure which may be alicyclic, heterocyclic, aromatic or macrocyclic and have densities between 0.950 g/cm$^3$ and 1.500 g/cm$^3$, preferably between 1.000 g/cm$^3$ and 1.500 g/cm$^3$ and more preferably between 1.050 g/cm$^3$ and 1.400 g/cm$^3$, with ClogP values between 1.00 and 6.00, preferably between 1.50 and 5.00 and more preferably between 2.00 and 5.00 and even more preferably between 2.00 and 4.50. Preferably high density cyclic aromachemical materials useful for the purposes of the invention have molecular weights greater than 150 mass units and below 300 mass units. Table 1 below, lists examples of a number of common high density cyclic aromachemical materials appropriate for the purposes of the present invention. This list is intended to exemplify fragrance materials and not to be comprehensive, nor in any way limiting on the invention.

TABLE 1

Examples of Cyclic Aromachemical Materials

| Compound | CAS Number | Density | ClogP |
|---|---|---|---|
| ALLYL PHENOXY ACETATE | 007493-74-5 | 1.100 | 2.45 |
| AMYL SALICYLATE | 2050-08-0 | 1.065[c] | 4.45 |
| ISO AMYL SALICYLATE | 87-20-7 | 1.053[c] | 4.45 |
| ANISYL PROPIONATE | 007549-33-9 | 1.07[d] | 2.41 |
| BENZOPHENONE | 119-61-9 | 1.067[c] | 3.18 |
| BENZYL ACETATE | 140-11-4 | 1.055 | 1.96 |
| BENZYL BENZOATE | 120-21-4 | 1.112 | 3.70 |
| BENZYL SALICYLATE | 000118-58-1 | 1.176 | 4.16 |
| ISO BORNYL ACETATE | 125-12-2 | 0.986[c] | 4.04 |
| CEDANOL | 7070-15-7 | 0.986[c] | 3.12 |
| CINNAMYL ACETATE | 000103-54-8 | 1.050 | 2.55 |
| CIS 3-HEXENYL SALICYLATE | 65405-77-8 | 1.059 | 4.50 |
| COUMARIN | 91-64-5 | 1.237[c] | 1.41 |
| CYCLOHEXYL SALICYLATE | 025485-88-5 | 1.112[a] | 4.37 |
| CYCLACET ™ (3a,4,5,6,7,7a-hexahydro-4,7-methano-1H-inden-5(or 6)-yl acetate) | 005413-60-5 | 1.071 | 2.88 |
| DIHYDROEUGENOL | 002785-87-7 | 1038[d] | 2.88 |
| DIHYDROISOJASMONATE | 37172-53-5 | 1.003[c] | 3.09 |
| DIMETHYL RESORCINOL | 000151-10-0 | 1055[d] | 2.15 |
| 3,4-DIMETHOXY TOLUENE | 000494-99-5 | 0.990 | 2.30 |
| DIPHENYL ETHER | 000101-84-8 | 1.075 | 4.24 |
| ETHYL ANISATE | 000094-30-4 | 1.103[d] | 2.81 |
| ETHYL BENZOATE | 000093-89-0 | 1.050 | 2.64 |
| ETHYL 4-GUAIACOL | 002785-89-9 | 1.050 | 2.35 |
| ETHYL 3-PHENYL GLYCIDATE | 000121-39-1 | 1.102 | 2.43 |
| ETHYL 3-METHYL-3-PHENYL GLYCIDATE | 77-83-8 | 1.094[c] | 2.95 |
| ETHYL SALICYLATE | 000118-61-6 | 1.130 | 2.86 |
| ETHYL VANILLIN | 121-32-4 | 1.130 at 80° C. | 1.81 |
| ETHYLENE BRASSYLATE | 105-95-3 | 1.018[c] | 3.02 |
| EUGENOL | 000097-53-0 | 1.070 | 2.40 |
| EUGENYL ACETATE | 000093-28-7 | 1.055 | 2.30 |
| HELIOBOUQUET | 001205-17-0 | 1.163 | 2.37 |
| HELIOTROPINE | 120-57-0 | 1.267[c] | 1.76 |
| HELIOTROPYL ACETATE | 326-61-4 | 1.24[c] | 1.78 |
| INDOLE | 000120-72-9 | 1.086[b] | 2.13 |
| ISO BUTYL SALICYLATE | 000087-19-4 | 1.060 | 3.79 |
| ISO EUGENYL PHENYL ACETATE | 000120-24-1 | 1.119[d] | 4.33 |
| ISO EUGENOL | 000097-54-1 | 1.099[c] | 2.58 |
| MAGNOLIA INDENE | 027606-09-3 | 1.087 | 2.45 |
| 4-METHOXY ACETOPHENONE | 000100-06-1 | 1.082 | 1.80 |
| METHYL BENZOATE | 000093-58-3 | 1.089 | 2.11 |
| METHYL CINNAMATE | 001754-62-7 | 1.057[c] | 2.46 |
| METHYL SALICYLATE | 000119-36-8 | 1.180 | 2.33 |
| 2-METHYL-4-PROPYL-1,3-OXATHIANE | 59323-76-1 | 1.050[c] | 1.22 |
| PHENYLACETALDEHYDE GLYCERYL ACETAL | 29895-73-6 | 1.157 | 1.08 |
| PHENYL BENZOATE | 000093-99-2 | 1.230 | 3.04 |
| 2-PHENYLETHYL ACETATE | 000103-45-7 | 1.088 | 2.28 |
| PHENYL ETHYL BENZOATE | 000094-47-3 | 1.093[d] | 4.22 |
| PHENYL ETHYL PHENYL ACETATE | 000102-20-5 | 1.082[d] | 3.92 |
| PHENYL ETHYL SALICYLATE | 000087-22-9 | 1.154[d] | 4.43 |
| PHENYL SALICYLATE | 000118-55-8 | 1.260 | 3.84 |
| PHENOXY ETHYL ISO BUTYRATE | 000103-60-6 | 1.044[d] | 2.92 |
| VANILLIN | 121-33-5 | 1.056[c] | 1.28 |
| VANILLIN ISOBUTYRATE | 20665-85-4 | 1.12[d] | 1.72 |
| ETHYL MALTOL | 4940-11-8 | 1.379[c] | 1.13 |
| WATERMELON KETONE | 28940-11-6 | 1.161 at 40° C. | 1.80 |

[a]Kao MSDS for cyclohexyl salicylate
[b]measured at 60° C. reported in JCS Perkin Trans 2 p199-200 (2002)
[c]Beilstein
[d]Sigma-Aldrich catalogue 2008-2009 and references therein.
Cyclacet is a trade mark of International Flavors and Fragrances.

An especially preferred group of cyclic aromachemical materials for inclusion into capsules cores includes: benzyl acetate, benzophenone, benzyl salicylate, c is 3-hexenyl salicylate, coumarin, cyclohexyl salicylate, Cyclacet™, ethylvanillin, eugenol, heliotropine, indole, isoeugenol, methyl anthranilate, methyl benzoate, oxane (2-methyl-4-propyl-1, 3-oxathiane), 2-phenylethanol, vanillin, vanillin isobutyrate, watermelon ketone and mixture thereof.

High density cyclic aromachemical materials must comprise 20% to 100% by weight of the fragrance compositions, preferably they should comprise 30 to 100% by weight of the fragrance composition, more preferably they should comprise 40 to 100% by weight of the fragrance composition, even more preferably they should comprise 50 to 100% by weight of the fragrance composition and especially preferably they should comprise 60 to 100% by weight of the fragrance composition and more preferably they should comprise 75 to 100% by weight of the fragrance composition.

Essential oils which have a density greater than 0.950 g/cm$^3$ and contain more than 50% by weight of cyclic aromachemical materials with ClogP values between 1.00 and 6.00 are considered to be also cyclic aromachemical materials in their entirety and not just the proportion of cyclic aromachemical materials.

Fragrance Materials (Category B)

An optional but often desirable feature of the invention is the inclusion into the microcapsule core of 0 to 80%, preferably 5 to 60%, more preferably 10 to 55%, more preferably 20 to 55% or even more preferably 30 to 55% by weight of one or more category B fragrance materials.

Category B fragrance materials are characterized in that they may or may not possess a cyclic unit in their molecular structure but their densities are below 0.950 g/cm$^3$ at 20° C. or such higher temperature that the density can properly be measured. They also conform to the above definition of fragrance materials in that they have ClogP values between 1.00 and 6.00 and molecular weights between 75 amu and 325 amu. Table 2 below lists examples of a number of common fragrance materials which may or may not have cyclic units as part of the molecular structure, have densities between 0.630 and 0.950 g/cm$^3$ and ClogP values between 1.00 and 6.00. This list is intended to exemplify fragrance materials of category B and not to be comprehensive, nor in any way limiting on the invention. The mixtures thereof are also preferable.

TABLE 2

Examples of fragrance materials of category B

| COMPOUND | CAS NUMBER | DENSITY | ClogP |
| --- | --- | --- | --- |
| ALLYL CAPROATE | 123-68-2 | 0.887 | 3.07 |
| CITRONELLOL | 106-22-9 | 0.855 | 3.25 |
| GAMMA DECALACTONE | 706-14-9 | 0.948 | 2.36 |
| DIHYDROMYRCENOL | 18479-58-8 | 0.834 | 3.033 |
| CIS 3-HEXENYL ACETATE | 35926-04-6 | 0.897 | 2.32 |
| LIMONENE | 5989-27--5 | 0.844 | 4.35 |
| LINALOOL | 78-70-6 | 0.87 | 2.75 |
| PRENYL ACETATE | 1191-16-8 | 0.917 | 1.88 |
| BUTYL CYCLOHEXYL ACETATE | 88-41-5 | 0.937 | 4.06 |

Preferably fragrance materials of category A and Category B comprise at least 3 kinds of fragrance materials in total, more preferably 10 kinds of fragrance materials in total, and further more preferably 15 kinds of fragrance materials in total.

High Density Oil Soluble Organic Compounds (Category C)

An optional but often desirable feature of the invention is the inclusion into the microcapsule core of 0 to 50%, preferably 5 to 50%, more preferably 10 to 50% and even more preferably 20 to 50% by weight of one or more high density oil soluble organic compounds. "Organic" and "high density" have the same meanings as previously defined in the specification. Oil soluble in the context of the present specification means materials which have solubility greater than 1.5 g per 100 g of diethyl phthalate at 20° C. after 48 hours. Some high density oil soluble organic compounds may have cyclic structures within their molecular formulae but they need not do so. Generally the high density oil soluble organic compounds are not commonly used as fragrance ingredients, although they may have an odour and may be used in fragrance compositions. They may also be used as diluents in fragrances or may be used as ingredients in food products. High density oil soluble organic compounds are further defined as follows.

i) High Density Oil Soluble Organic Polyester Compounds (Category Ci)

"Polyester" means the compounds process at least two ester groups. Moreover the high density oil soluble polyester compounds should have a molecular weight between 100 amu and 1500 amu, preferably between 125 amu and 1000 amu and more preferably between 150 and 750 amu and contain at least 2 ester groups per molecule and have densities between 0.950 g/cm$^3$ and 1.500 g/cm$^3$, preferably between 1.000 g/cm$^3$ and 1.500 g/cm$^3$ even more preferably between 1.050 g/cm$^3$ and 1.500 g/cm$^3$ and especially preferably between 1.100 g/cm$^3$ and 1.500 g/cm$^3$ and especially preferably between 1.150 g/cm$^3$ and 1.400 g/cm$^3$ or are compounds of the following formulae:

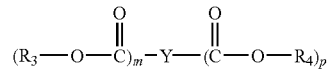

in which:
R$_3$ and R$_4$, identical or different, represent a linear or branched (C$_1$-C$_6$)alkyl;
Y represents a (C$_2$-C$_6$)alkenylene or alkynylene, optionally substituted by one or several hydroxyl or phenyl groups;
m and p, identical or different, are integers from 1 to 4.

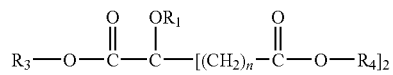

in which:
R$_1$ represents a hydrogen atom or a linear or branched (C$_1$-C$_6$)alkylcarbonyl;
R$_3$ and R$_4$, identical or different, represent a linear or branched (C$_1$-C$_6$)alkyl;
n is 0 to 3, preferably 1 to 3.
In the above formulae, R$_3$ and R$_4$ are preferably (C$_1$-C$_3$) alkyl groups, R$_1$ is preferably a (C$_1$-C$_3$)alkylcarbonyl and Y is preferably a (C$_2$-C$_3$)alkenylene or alkynylene.

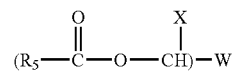

in which:
X represents H, a $(C_1-C_3)$alkyl, $CH(R_6)OCOR_7$;
W represents H, a $(C_1-C_3)$alkyl, $CH(R_6)OCOR_7$, $(CH_2)$ $CH(R_6)OCOR_7$;
$R_5$ represents a linear or branched $(C_1-C_3)$alkyl;
$R_6$ and $R_7$, identical or different, represent H or a linear or branched $(C_1-C_3)$alkyl;
n is an integer from 1 to 4, provided that at least X or W is an ester group.

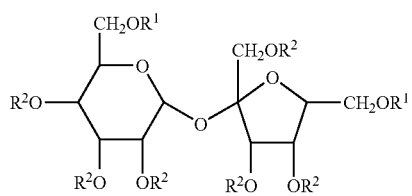

in which:
$R_1$ and $R_2$, identical or different represent a —CO—R group in which R is a linear or branched $(C_1-C_6)$alkyl group.

Table 3 lists a number of high density oil soluble organic ingredients which are intended to exemplify the range of high density organic oil soluble polyester materials but not to be comprehensive, nor in any way limiting on the invention. The mixtures thereof are also preferable.

TABLE 3

Examples of High Density Organic Oil Soluble Polyester Compounds (Category Ci)

| COMPOUNDS | CAS No | Density* (g/cm³) |
|---|---|---|
| ACETYL TRIETHYL CITRATE | 77-89-4 | 1.136 |
| DIETHYL MALEATE | 141-05-9 | 1.064 |
| DIETHYL MALONATE | 105-53-3 | 1.055 |
| DIETHYL ADIPATE | 141-28-6 | 1.009 |
| DIMETHYL ADIPATE | 627-93-0 | 1.062 at 20° C. |
| DIETHYL SUCCINATE | 123-25-1 | 1.047 |
| DIETHYL TARTARATE | 87-91-2 | 1.204 |
| DIETHYL PHTALATE | 84-66-2 | 1.12 |
| DIMETHYL TEREPHTHALATE | 120-61-6 | 1.20 |
| GLYCERYL TRIACETATE | 102-76-1 | 1.21 |
| PROPYLENE GLYCOL DIACETATE | 623-84-7 | 1.050** |
| SUCROSE OCTA-ACETATE | 126-14-7 | 1.28 |
| SUCROSE DIACETATE HEXAISOBUTYRATE | 27216-37-1 | 1.15 |
| GLYCERYL TRIPROPIONATE | 139-45-7 | 1.08 |
| TRIETHYL CITRATE | 77-93-0 | 1.137 |

*reported in Sigma Aldrich Catalogue 2008-2009
**reported in Dow Chemicals technical datasheet at 25° C. for Dowanol PGDA.

High density organic oil soluble polyester organic compounds must however be safe for use in personal care and cosmetic products and they must also be safe to discharge into the environment. For this reason, halogens containing organic materials are not considered as suitable for incorporation into microcapsules. Examples of preferred high density organic oil soluble polyester compounds include sucrose octa-acetate, glyceryl triacetate, glyceryl tripropionate, diethyl tartarate, triethyl citrate and acetyl triethyl citrate.

ii) High Density Organic Polymers (Category Cii)

Organic polymers with molecular weights between 2,000 amu and 250,000 amu preferably between 5,000 amu and 100,000 amu, which contain at least 19% and preferably more than 25% by weight of either one or a mixture of oxygen, nitrogen and sulphur atoms calculated on the monomer molecular weight, or in the case of copolymers, on the weight averaged molecular weight for any mixture of monomers prior to the polymerisation reaction and have densities between 1.000 g/cm³ and 1.500 g/cm³, preferably between 1.050 g/cm³ and 1.500 g/cm³ even more preferably between 1.100 g/cm³ and 1.500 g/cm³ and especially preferably between 1.150 g/cm³ and 1.400 g/cm³ may be included in the fragrance composition at 0 to 50% preferably 10 to 50% and more preferably 20 to 50% by weight for inclusion into the fragrance composition for encapsulation.

For high density organic ingredients which are polymers (group Cii) the monomer from which the polymer is produced should preferably contain at least 19% by weight of any combination of oxygen, nitrogen or sulphur compounds atoms, preferably more than 25% of any combination of these atoms and more preferably more than 30% of any combination of oxygen, nitrogen or sulphur atoms. The polymers should preferably have a molecular weight range between 2000 and 250,000 amu preferably between 5000 and 200,000 amu and more preferably between 10,000 and 100,000 amu. Furthermore the monomers comprise only atoms from among, but not necessarily all of, carbon, hydrogen, oxygen, nitrogen and sulphur atoms. The monomers should not contain any strongly ionising groups such as sulphonate or sulphate salts or quaternary ammonium salts. The polymers may be prepared by any standard means such as radical polymerisation of unsaturated monomers such as vinyl or acrylic monomers e.g. vinyl acetate to produce polymers such as polyvinyl acetates or polyacrylamides or polyacrylates. Alternatively the polymers may be produced by condensation reactions such as those leading to polyethers or polyesters, such as polypropylene glycol or polyterephthalate esters or polyamides.

Polymers which contain more than one monomer type are also considered part of the invention provided the polymer preferably contains at least 19% of any combination of oxygen, nitrogen or sulphur atoms averaged over the weight percentage of the monomers, preferably more than 25% of any combination of oxygen nitrogen and sulphur atoms and more preferably more than 30% of any combination of oxygen, nitrogen or sulphur atoms.

Table 4 lists a number of high density organic polymers which are intended to exemplify the range of materials but not to be comprehensive, nor in any way limiting on the invention. Some of the data is quoted in ranges as the densities of polymers may vary depending on the history of the sample. The data is taken from the Polymer Handbook 4$^{th}$ Edition Ed by J Brandup et al published by J Wiley and Sons in 2005 (ISBN 978-0-471-16628-3).

TABLE 4

Examples of High Density Organic Polymer

| Polymer | Density (g/cm³) |
|---|---|
| CELLULOSE ACETATE | 1.22-1.34 |
| POLYSTYRENE | 1.04-1.11 |
| POLYVINYL ACETATE | 1.19 |
| POLYAMIDE 6 | 1.24 |
| POLYMETHYLMETHACRYLATE | 1.17-1.20 |

Fragrance Solvents (Category Ciii)

It is common to use solvents within fragrances either as liquid solubilising agents for solid fragrance ingredients or as diluents for the more potent ingredients or to control the vapour pressure and evaporation characteristics of the fragrance. For the purpose of this specification fragrance solvents are defined as liquids at 25° C. which can be added at 50% by weight to a fragrance without substantially changing the fragrance note. Table 5 below lists a number of fragrance solvents which are intended to exemplify the range of solvents but not to be comprehensive, nor in any way limiting on the invention.

TABLE 5

Common Fragrance Solvents

| COMPOUNDS | CAS No | Density (g/cm³) |
|---|---|---|
| Dipropylene glycol | 25265-71-8 | 1.023* |
| Dowanol TPM | 25498-49-1 | 0.962** |
| Propylene Glycol | 57-55-6 | 1.036* |

*reported in Sigma Aldrich Catalogue 2008-2009
**densities from Dow Chemical company technical datasheets at 25° C.

High density oil soluble organic materials may also comprise mixtures of materials from categories Ci), Cii) and Ciii) in any proportions.

Other Solvents (Category D)

The fragrance composition for encapsulation of the invention can also optionally comprise one or more solvents which do not fall under category Ciii) defined above. Table 5a below lists a number of such solvents, having a density usually above 0.800 g/cm³ and below 0.950 g/cm³.

TABLE 5a

Other Solvents

| COMPOUNDS | CAS No | Density (g/cm³) |
|---|---|---|
| 3-methoxy-3-methylbutan-1-ol | 56539-66-3 | 0.926 at 20° C. |
| Dowanol PM | 107-98-2 | 0.916** |
| Dowanol DPM | 34590-94-8 | 0.948** |
| Dipropylene Glycol nButyl ether | 29911-28-2- | 0.907** |
| Isopar L | N/A | 0.853*** |
| Isopropyl myristate | 110-27-0 | 0.853* |

*reported in Sigma Aldrich Catalogue 2008-2009
**densities from Dow Chemical company technical datasheets at 25° C.
***Isopar L is a registered trade mark of Exxon Mobil Chemicals the density is reported as measured at 15° C.

When present, materials of category D comprise 0 to 50%, preferably 5 to 50%, more preferably 10 to 50% and even more preferably 20 to 50% by weight of the fragrance composition for encapsulation. Needless to say, the sum of A), B), C) and D) then equals 100%. However, the combined amount of category C materials and category D materials cannot exceed 50% by weight of the composition.

Microcapsules

The fragrance composition of the invention is particularly appropriate for making encapsulated fragrance products or fragrance-containing core shell microcapsules. The term "microcapsule" is used herein in the broadest sense and includes the encapsulation of fragrance and other materials or actives in small capsules (i.e. microcapsules), typically having an average particle size between 1 micrometers and 500 micrometers preferably between 2 micrometers and 200 micrometers, more preferably between 5 micrometers and 100 micrometers and especially preferably between 10 micrometers and 50 micrometers. The average particle size can be determined in several different ways, however the preferred technique is by light scattering using a Malvern Mastersizer with the average particle size being taken as the median particle size D (0.5) value.

Core shell microcapsules typically comprise a spherical hollow shell of water insoluble or at least partially water insoluble material, typically polymer material, within which the fragrance and other material is contained. Microcapsules are described in the following patent applications or patents US 2003/215,417 A1; US 2003/216,488 A1; US 2003/165,692 A1; US 2004/071,742 A1; US 2004/071,746 A1; US 2004/072,719 A1; US 2004/072,720 A1; EP 1393706 A1; US 2003/203,829 A1; US 2003/195,133 A1; US 2004/087,477 A1; US 2004/106,536 A1; U.S. Pat. No. 6,200,949; U.S. Pat. No. 4,882,220; U.S. Pat. No. 4,917,920; U.S. Pat. No. 4,514,461; US RE 32,713; U.S. Pat. No. 4,234,627.

Microcapsules may be prepared using a range of conventional methods known to those skilled in the art for making core shell microcapsules, such as coacervation, interfacial polymerization, and polycondensation. See e.g., U.S. Pat. No. 3,516,941, U.S. Pat. No. 4,520,142, U.S. Pat. No. 4,528,226, U.S. Pat. No. 4,681,806, U.S. Pat. No. 4,145,184; GB 2,073,132; WO 99/17871; and MICROENCAPSULATION: Methods and Industrial Applications Edited by Benita and Simon (Marcel Dekker, Inc. 1996). It is recognized, however, that many variations with regard to materials and process steps are possible whilst still essentially manufacturing a core shell microcapsule. Non-limiting examples of materials suitable for making shell of the microcapsule include urea-formaldehyde, melamine-formaldehyde, phenol-formaldehyde, polymethacrylate esters, polyvinyl compounds, gelatin, carageenan, polyurethane, polyamides, or any combination of the above.

In one preferred embodiment of the invention, the shell of the microcapsules comprises predominantly an aminoplast resin. Methods for forming such shell microcapsules include polycondensation reactions. Aminoplast resins are the reaction products of one or more amines with one or more aldehydes, typically formaldehyde. Non-limiting examples of suitable amines include urea, thiourea, melamine and its derivatives, benzoguanamine and acetoguanamine and combinations of amines. Suitable cross-linking agents (e.g., toluene diisocyanate, divinyl benzene, butanediol diacrylate etc.) may also be used and secondary wall polymers may also be used as appropriate, e.g., anhydrides and their derivatives, particularly polymers and co-polymers of maleic anhydride as disclosed in US 2004/0,087,477 A1. In a preferred embodiment of the invention the shell of the microcapsules comprises urea-formaldehyde; melamine-formaldehyde; or combinations thereof and the resulting microcapsules are commonly known as aminoplast core shell microcapsules.

Those skilled in capsule manufacture will appreciate that there are many variations which may be introduced into the manufacture of core shell microcapsules such as varying ingredient proportions and/or process parameters but which still fall within the general description for core shell preparation as described in the present specification and the cited references. However one variation which may be noted is that of dissolving salts of alkali metals or ammonia and amine derivatives to the aqueous phase of the emulsion prior to the encapsulation reaction to help in the formation of a stable emulsion phase when less hydrophobic ingredients are present in the core composition. These salts may be of inorganic acids such as hydrochloric, sulphuric, phosphoric or nitric acids.

Without wishing to limit the patent in any way a typical process for preparing a capsule dispersion would include the following steps.

The preparation of an emulsion of the fragrance ingredients and any benefit agents or modifiers which may include emulsifying agents or emulsion stabilizers takes place under vigorous agitation.

The first step is the mixing of the above emulsion with melamine-formaldehyde resin (with a melamine:formaldehyde:methanol mixture in the approximate molar ratios 1:3:2 to 1:6:4) and an emulsifier. These monomers may be precondensed or the monomers may be used directly. Some of the melamine can be replaced by urea. In these polymers, the formaldehyde may be partially etherified preferably as the methyl ethers.

Preferably, the shell is constituted of 50 to 100% formaldehyde-melamine or formaldehyde-melamine-urea or formaldehyde-urea condensation polymers or partially corresponding etherified formaldehyde condensation polymers, preferably as the methyl ethers. The shell may be also constituted of 50 to 100% of methacrylate or urethane.

Then, acid is added to the above mixture to adjust to a pH of 3.5 to 6.5 and the temperature raised to 30 to 45° C. Stirring is allowed to proceed until the dispersion is oil free. Any acid which has no adverse properties may be used in this process, such as for example formic acid or acetic acid.

It is particularly advantageous if the capsules are cured by heating to a temperature between 60° C. to 100° C. for several hours under moderate stirring.

It is particularly advantageous if during the early phase of curing a further addition of urea, melamine or other amines, or mixtures thereof can be made to reduce the formaldehyde concentration in the finished dispersion, and increase the wall thickness.

Typically 10 to 30% additional melamine and/or urea can be added at this stage, and a particularly advantageous ratio is 5:1 to 1:1 melamine:urea.

Once curing is complete, the temperature is reduced to around 50° C., and the dispersion is neutralized before being adjusted to a pH around 9.5.

The microcapsules of the present invention, in one embodiment, are friable in nature. Friability refers to the propensity of the microcapsules to rupture or break open when subjected to direct external pressures or shear forces. For purposes of the present invention, the microcapsules utilized are "friable" if, while attached to fabrics treated therewith, they can be ruptured by the forces encountered when the microcapsules-containing fabrics are manipulated by being worn or handled (thereby releasing the contents of the microcapsules). In one embodiment, the core shell microcapsules typically have a mean external diameter in the range of from 1 micrometer to 500 micrometers, preferably from 5 micrometers to 200 micrometers, and more preferably from 5 micrometers to 100 micrometers, and especially preferably from 10 micrometers to 50 micrometers. The particle size distribution can be narrow, broad or multimodal.

The microcapsules of the present invention are distinguished from moisture-activated microcapsules, such as those microcapsules comprising of starch that burst upon contact with moisture such as those described in U.S. Pat. No. 5,246,603 which are not considered to be core shell microcapsules.

Liquid Household Laundry Personal Care and Cosmetic Products

The formulations and ingredients of liquid household, laundry and personal care and cosmetic products in which microcapsules containing fragrance compositions of the invention may be used are well known to those skilled in the art, reference may be made to the following works which are incorporated herein by reference:

Formulating Detergents and Personal Care Products A guide to Product Development by L. Ho Tan Tai, ISBN 1-893997-10-3 published by the AOCS Press. Also to Volume 67 of the Surfactant Science Series Liquid Detergents ISBN 0-8247-9391-9 (Marcel Dekker Inc), as well as to the following patents or patent applications:

Liquid Laundry Detergents:

U.S. Pat. No. 5,929,022, U.S. Pat. No. 5,916,862, U.S. Pat. No. 5,731,278, U.S. Pat. No. 5,470,507, U.S. Pat. No. 5,466,802, U.S. Pat. No. 5,460,752, and U.S. Pat. No. 5,458,810.

Shampoos and Hair Conditioners:

U.S. Pat. No. 6,162,423, U.S. Pat. No. 5,968,286, U.S. Pat. No. 5,935,561, U.S. Pat. No. 5,932,203, U.S. Pat. No. 5,837,661, U.S. Pat. No. 5,776,443, U.S. Pat. No. 5,756,436, U.S. Pat. No. 5,661,118, U.S. Pat. No. 5,618,523.

Liquid household, laundry and personal care and cosmetic products can have a range of densities typically 0.800 to 1.600 g/cm$^3$ more preferably for liquid compositions containing surfactants, emulsified oils, solvents and inorganic material either in solution or suspended in the formulation, 0.900 to 1.400 g/cm$^3$. Those which are predominantly aqueous compositions will tend to have densities close to 1.000 g/cm$^3$. The term predominantly aqueous liquid product means a product in which water is the largest ingredient by weight percentage. Typically predominantly aqueous compositions will contain water between 30% by weight and 95% by weight.

Some non-aqueous or low aqueous liquid product formulations contain substantial proportions of polar solvents such as alcohols and glycols consequently their densities may be greater than 1.000 g/cm$^3$ as illustrated in table 6.

Most aqueous liquid fabric softeners which may be termed fabric conditioners contain predominantly water and cationic surfactant and their densities are less than 1.000 g/cm$^3$ especially the concentrated formulations which contain a higher concentration of cationic surfactant. Thus aqueous liquid rinse conditioners which are defined as products used in the rinsing step of domestic fabric laundering which contain more than 50% water and between 4% and 30% of a softening cationic surfactant are excluded from this invention. Table 6 below contains some illustrative examples of the densities of some commercial brands of liquid household, laundry, personal care and cosmetic products. Once again the list is illustrative and is neither meant to be comprehensive nor limiting on the invention.

TABLE 6

Densities of Commercial Liquid Household Laundry Personal Care and Cosmetic Products

| Product | Density (g/cm$^3$) | Viscosity at 25° C. | Manufacturer |
|---|---|---|---|
| European Ariel Concentrated Detergent Liquid | 1.070 | | Procter and Gamble |
| European Ariel Standard Detergent Liquid | 1.040 | 338 | Procter and Gamble |

TABLE 6-continued

Densities of Commercial Liquid Household Laundry Personal Care and Cosmetic Products

| Product | Density (g/cm³) | Viscosity at 25° C. | Manufacturer |
|---|---|---|---|
| European Aerial Hydroactiv | 1.050 | | Procter and Gamble |
| Dash/Bold Concentrated Liquid | 1.100 | | Procter and Gamble |
| Dash/Bold Standard Liquid | 1.070 | | Procter and Gamble |
| All Small and Mighty | 1.050-1.070 | | Unilever |
| Comfort Pearls | 1.042 | | Unilever |
| Persil Liquid tablet | 1.026 | | Unilever |
| Le Chat Concentre Gel Fr | 1.070-1.080 | 360 | Henkel |
| Super Croix Standard Liquid | 1.020-1.030 | | Henkel |
| Persil Colour Gel (De) | 1.070-1.080 | | Henkel |
| Persil Kraft Gel Concentrate (De) | 1.070-1.080 | 874 | Henkel |
| US Tide 2X Concentrate Fragrance Free Sensitive Skin | 1.081 | 400 | Procter and Gamble |
| US Tide Regular Fragrance Free Sensitive Skin | 1.048 | | Procter and Gamble |
| US Tide 2X Concentrate HE | 1.040-1.090 | | Procter and Gamble |
| US 2X Clean Burst Concentrate | 1.031 | | Arm & Hammer |
| US Fresh Scent and Oxy Clean | 1.042 | | Arm & Hammer |
| Japanese Attack Bio Gel | 1.027 | | Kao |
| Japanese Liquid Top | 1.039 | | Lion |
| Japanese Aerial Ion Power | 1.043 | | Procter and Gamble |
| Dove Cool Moisture Shampoo | 1.054 | | Unilever |
| Dove Douche Soin de Beaute (Fr) | 1.034 | 11800 | Unilever |
| Palmolive Tahiti Homme Shampoo et Douche (Fr) | 1.018 | | Colgate |
| Palmolive hand wash | 1.042 | | Colgate |

As stated earlier microcapsules, having an average particle size greater than 5 microns, incorporated into liquid products have a tendency to separate either by creaming or settling, especially on extended storage or at elevated temperatures e.g. at 40° C. However for liquid products which have high viscosities and particularly if they have high viscosities at very low shear rates the viscosity may prevent separation, from the equation it is apparent that there is a relationship between product viscosity and the density difference between the capsule and liquid product. The greater the difference in densities the more viscous a product needs to be to suspend the capsules. This is easily illustrated by products which are sufficiently viscous that they can suspend air bubbles for quite long periods. Temperature can affect the viscosity of liquid products. Products which have high viscosities at ambient temperatures of 20° C. may have much lower viscosities when stored at higher temperatures. Table 7 below shows the effect of shear rate and temperature on the viscosity of a liquid detergent Persil Kraft Gel Concentrate made by Henkel in Europe. Not only does the viscosity drop on increasing the shear but the viscosity is much lower when measured at 37° C. It is also known for the viscosities of some products to thicken when stored at 37° C. or above temperatures for a period of time.

TABLE 7

Viscosity of Persil Kraft Gel Concentrated Liquid Laundry Detergent

| Spindle speed rpm | Viscosity at 25° C. (mPas) | Viscosity at 37° C. (mPas) |
|---|---|---|
| 0.3 | 6600 | 1130 |
| 0.6 | 3600 | 675 |
| 1.5 | 2100 | 570 |
| 3 | 1610 | 525 |
| 6 | 1280 | 493 |
| 12 | 1060 | Not measured |
| 30 | 874 | Not measured |

Ambient temperatures vary across the world and due to changing seasons so for a capsule to remain suspended it is required for the viscosity to remain high unless the densities are well matched. Hence it is preferable if the liquid household, laundry, personal care or cosmetic products into which microcapsules containing fragrance compositions of this invention are introduced have viscosities of between 10 and 5,000 mPas, preferably between 10 and 2,500 mPas, more preferably between 20 and 2,000 mPas, and even more preferably between 50 and 1500 mPas measured at either 25° C. or at 40° C. whichever gives the lower value using a Brookfield LVT viscometer with spindle No 31 at 30 rpm. For some formulations the product viscosity may change during prolonged storage at elevated temperature. Thus the values given above should not only be applied to freshly made samples but also to those that have been stored for 12 weeks at 40° C.

The liquid household, laundry, personal care or cosmetic products into which microcapsules containing fragrance compositions of this invention are introduced, may contain a surfactant. This is typically used in an amount of at least 2% by weight of the product, preferably in the range of from 2% to 40% by weight.

Microcapsule fragrance dosage into liquid products depends on the total payload of benefit agent to be delivered. Various aspects influence the dosage: the microcapsule dispersion concentration, the proportion of fragrance within the microcapsule and the amount of material necessary to create the effect desired. Measured as dry weight of microcapsules after removal of all water and solvents from the microcapsule preparation the dosage of microcapsule into liquid products should be in the range from 0.01 to 10% by weight of the liquid product composition, preferably from 0.05% to 2.5% by weight, more preferably from 0.1 to 1.25% by weight of the composition. The microcapsules may be incorporated into the products by any conventional means usually as a liquid dispersion added at a suitable stage in the process but usually after any high shear mixing.

The present invention will be now disclosed in more details by the following illustrative, but not limiting, examples.

EXAMPLES

Example 1

Preparation of Microcapsules

A 2l cylindrical stirring vessel was fitted with an adjustable disperser having a standard commercial dispersion disk with a diameter of 50 mm.

It was charged in succession with:
400 g of a Fragrance composition of the invention
86 g of a 70% strength aqueous solution of a methylated melamine-formaldehyde resin (molar ratio melamine:formaldehyde:methanol 1:3.9:2.4) with a Brookfield viscosity of 275 mPas and a pH of 8.5;
80 g of a 20% strength solution of poly-2-acrylamido-2-methylpropanesulfonic acid sodium salt;
350 g of water;
15 g of 10% strength by weight aqueous formic acid solution.

This charge was processed to a microcapsule dispersion by adjusting the stirring speed to a peripheral speed of approximately 20 ms$^{-1}$. The temperature was held at about 35° C.

After 60 minutes, the dispersion was oil-free; a particle size of about 20 to 30 μm had been established. The stirring speed of the dispersion disk was then reduced to a level sufficient for uniform circulation of the vessel contents.

A cure temperature of 80° C. was set, and once reached by injection of hot steam, a feed of a 27% suspension of melamine-urea (ratio 2.5:1, melamine:urea) in formic acid (to adjust pH to pH 4.5) was added to the dispersion of the preformed microcapsules with a constant mass flow rate and was metered in over the course of an hour. A total of 46 g of the suspension of melamine-urea was metered in.

A cure phase of 120 min ensued at 90° C.

After the dispersion had been cooled to about 55° C., it was neutralized with diethanolamine to pH 7.0 and adjusted to a pH of 8.5 using ammonia.

A dispersing agent was added to give uniform microcapsule dispersion with solids content of 50% and a viscosity of 83 mPas.

Example 2

Fragrance Composition 1

Table 8 below gives a fragrance composition comprising 4 kinds of fragrance materials, all of which have densities greater than 0.950 g/cm$^3$ and ClogPs between 1.00 and 5.00. So fragrance composition 1 which has a density of 1.0553 g/cm$^3$ contains 100% of high density cyclic aromachemical materials and is suitable for encapsulation by the procedure of example 1 or it may be treated as an accord and blended with up to 80% by weight of low density fragrance materials before encapsulation.

TABLE 8

| Fragrance Composition 1 | | | | | |
|---|---|---|---|---|---|
| Ingredient | CAS No | % by weight | Mol Wt | Density g/cm$^3$ | ClogP |
| Dihydro-isojasmonate | 37172-53-5 | 30 | 226.32 | 0.996$^a$ | 3.09 |
| Diphenyl ether | 101-84-8 | 10 | 170.21 | 1.073$^b$ | 4.24 |

TABLE 8-continued

| Fragrance Composition 1 | | | | | |
|---|---|---|---|---|---|
| Ingredient | CAS No | % by weight | Mol Wt | Density g/cm$^3$ | ClogP |
| 3-(3,4-methylene-dioxyphenyl)-2-methylpropanal | 1205-17-0 | 20 | 192.21 | 1.162$^b$ | 2.37 |
| Ethylene Brassylate | 105-95-3 | 40 | 270.36 | 1.042$^b$ | 3.02 |

$^a$measured at 20° C.
$^b$from Sigma Aldrich Catalogue 2008-2009

Example 3

Fragrance composition 2

Table 9 provides a further example of a fragrance composition suitable for encapsulation by a condensation reaction as in example 1. Fragrance composition 2 comprises 81% of cyclic aromachemical materials which have densities greater than 0.950 g/cm$^3$ and ClogPs between 1.00 and 5.00 and 15% of a high density oil soluble organic compound. The density of this fragrance composition is 1.1549 g/cm$^3$.

Within table 9 and in subsequent examples ingredients of the compositions are assigned to the categories A, B, C or D to more easily illustrate the invention:

TABLE 9

| Fragrance Composition 2 | | | |
|---|---|---|---|
| Ingredient | CAS No | % by weight | Category of material |
| Heliotropyl acetate | 326-61-4 | 50 | A |
| Amyl salicylate | 2050-08-0 | 25 | A |
| Ethyl vanillin | 121-32-4 | 6 | A |
| Cis 3-hexenyl acetate | 3681-71-8 | 4 | B |
| Triethyl citrate | 77-93-0 | 15 | C |

Example 4

Fragrance composition 3

Fragrance composition 3 in table 10 below gives a fragrance composition which is suitable for incorporation into a microcapsule by the procedure of example 1. Fragrance composition 3 has a density of 0.9384 g/cm$^3$ and contains 5 kinds of cyclic high density fragrance materials which comprise 45.65% of the fragrance composition by weight.

TABLE 10

| Fragrance Composition 3 | | | |
|---|---|---|---|
| Compound | CAS number | % by weight | Category of material |
| Allyl caproate | 123-68-2 | 0.050 | B |
| Camphor gum powder | 464-49-3 | 2.00 | A |
| Cedanol | 7070-15-7 | 12.50 | A |
| Citronellyl nitrile | 51566-62-2 | 3.75 | B |
| Diphenyl oxide | 101-84-8 | 6.25 | A |
| Dipropylene Glycol | 25265-71-8 | 0.50 | C |
| 1-(5,5-dimethyl-1-cyclohexen-1-yl)-4-penten-1-one (Dynascone ™) | 56973-85-4 | 0.50 | B |
| 2-methyl-4-(2,2,3-trimethyl-3-cyclopentenyl)-2-buten-1-ol (Santaliff ™) | 28219-60-5 | 16.25 | B |

TABLE 10-continued

Fragrance Composition 3

| Compound | CAS number | % by weight | Category of material |
|---|---|---|---|
| β-Ionone | 14901-07-6 | 6.25 | B |
| Isobornyl acetate | 125-12-2 | 18.00 | A |
| Ethyl 2-methyl pentanoate | 39255-32-8 | 9.40 | B |
| Limonene |  | 9.40 | B |
| Phenyl acetaldehyde DMA | 101-48-4 | 6.90 | A |
| 3 Pentanol 2,2,4-trimethyl-1-[(2methyl-2-propenyl)oxy] (Polymeflor ™) | 526218-21-3 | 6.25 | B |
| Rose oxide | 3033-23-6 | 2.00 | B |

Example 5

Fragrance compositions 4 to 10

Core compositions for encapsulation may be formulated as in table 11 below which shows how the density of the core composition can be varied by adding different proportions of high density oil soluble organic ingredients to fragrance composition 3 to increase the density and to match the density more closely to that of a target liquid consumer product.

TABLE 11

Fragrance Compositions

|  | Wt % Fragrance Composition 3 | Wt % Sucrose Octaacetate | Wt % Triethyl citrate | Density of composition |
|---|---|---|---|---|
| Fragrance Composition 3 | 100 | 0 | 0 | 0.938 |
| Fragrance Composition 4 | 97 | 3 | 0 | 0.946 |
| Fragrance Composition 5 | 91 | 9 | 0 | 0.961 |
| Fragrance Composition 6 | 87.5 | 12.5 | 0 | 0.977 |
| Fragrance Composition 7 | 70 | 30 | 0 | 1.019 |
| Fragrance Composition 8 | 85 | 0 | 15 | 0.964 |
| Fragrance Composition 9 | 70 | 0 | 30 | 0.990 |
| Fragrance Composition 10 | 50 | 0 | 50 | 1.028 |

Example 6

Fragrance Composition 11

A fragrance composition suitable for incorporating into a microcapsule core composition is formulated as in table 12 below.

TABLE 12

Fragrance Composition 11

| Compound | CAS number | Wt % | Category of material |
|---|---|---|---|
| Allyl caproate | 123-68-2 | 0.05 | B |
| Benzyl Salicylate | 118-58-1 | 30 | A |
| Camphor gum powder | 464-49-3 | 1.5 | A |
| Cedanol | 7070-15-7 | 8.75 | A |
| Citronellyl nitrile | 51566-62-2 | 2.60 | B |
| Diphenyl oxide | 101-84-8 | 4.30 | A |
| Dipropylene Glycol |  | 0.35 | C |
| 1-(5,5-dimethyl-1-cyclohexen-1-yl)-4-penten-1-one (Dynascone ™) | 56973-85-4 | 0.35 | B |

TABLE 12-continued

Fragrance Composition 11

| Compound | CAS number | Wt % | Category of material |
|---|---|---|---|
| 2-methyl-4-(2,2,3-trimethyl-3-cyclopentenyl)-2-buten-1-ol (Santaliff ™) | 28219-60-5 | 11.50 | B |
| β-Ionone | 14901-07-6 | 4.30 | B |
| Isobornyl acetate | 125-12-2 | 12.50 | A |
| Ethyl 2 methyl pentanoate | 39255-32-8 | 6.50 | B |
| Limonene |  | 6.50 | B |
| Phenyl acetaldehyde DMA | 101-48-4 | 5.0 | A |
| 3-pentanol-2,2,4-trimethyl-1-[(2methyl-2-propenyl)oxy] (Polymeflor ™) | 526218-21-3 | 4.40 | B |
| Rose oxide | 3033-23-6 | 1.40 | B |

Fragrance composition 11 comprises 62.05% of category A materials and has a density of 0.9973 g/cm$^3$. This fragrance composition was encapsulated into a formaldehyde melamine core shell microcapsule by the procedure of example 1. The final composition was TAKAPS 47.

Example 7

Fragrance composition 12

A further example of a fragrance composition of the invention which includes an essential oil is given in table 13 below

TABLE 13

Fragrance Composition 12

| Ingredient | CAS No | % by weight | Category of material |
|---|---|---|---|
| Amyris oil | 8015-65-4 | 21.44 | A (See table 14) |
| Benzyl acetate | 140-11-4 | 7.16 | A |
| Cedryl methyl ether | 19870-74-7 | 2.30 | A |
| Cedrenyl acetate | 77-54-3 | 2.0 | A |
| Dihydroisojasmonate | 37172-53-5 | 13.24 | A |
| Ethyl vanillin | 121-32-4 | 1.85 | A |
| 2-Heptylcyclopentanone | 137-03-1 | 1.43 | B |
| Heliotropine | 120-57-0 | 11.08 | A |
| Undecalactone gamma | 104-67-6 | 1.43 | B |
| (1,7,7-trimethylbicyclo[2,2,1]hept-2-yl)cyclohexanol (Santalex T ™) | 68877-29-2 | 4.07 | B |
| Ethylene brassylate | 105-95-3 | 27.79 | A |
| Triethyl citrate | 77-93-0 | 5.66 | C |
| Isopropyl myristate | 110-27-0 | 0.55 | D |

The major constituents of Amyris oil are listed in table 14 below which accounts for 70.3% of the constituents of Amyris oil. The oil used had a density of 0.959 g/cm$^3$ and the major components contain alicyclic rings within their chemical structures and have ClogP values greater than 1.5 but below 6.00. Thus the Amyris oil contributes high density components of the invention to the fragrance composition. Seven other high density ingredients with ClogP values between 1.50 and 6.00 and one high density non fragrance ingredient (triethyl citrate) bring the combined total percentage of high density ingredients to 93.07% by weight of the fragrance composition. This fragrance composition has a density greater than 0.950 g/cm$^3$ and is suitable for encapsulation by the method of example 1.

TABLE 14

Major Components of *Amyris* Oil

| Ingredient | CAS No | % by weight | Mol Wt | ClogP |
|---|---|---|---|---|
| Valerianol | 20489-45-6 | 21.5 | 222.4 | 4.62 |
| 7-epi-α-eudesmol | 123123-38-6 | 10.7 | 222.4 | 4.69 |
| Elemol | 639-99-6 | 9.10 | 222.4 | 4.75 |
| β-eudesmol | 473-15-4 | 7.9 | 222.4 | 4.68 |
| γ-Eudesmol | 1209-71-8 | 6.6 | 222.4 | 4.86 |
| α-eudesmol | 473-16-5 | 4.80 | 222.4 | 4.68 |
| β-sesqui-phellandrene | 20307-83-9 | 4.70 | 204.3 | 4.70 |
| Selina-3,7(11)diene* | 6813-21-4 | 2.50 | 204.3 | 6.73 |
| Zingiberene* | 495-60-3 | 2.50 | 204.3 | 6.60 |

*Zingiberene and Selina-3,7(11)diene have ClogP values outside the 1.00 to 6.00 range

Example 8

Storage Stability

This example compares the storage stability of microcapsules containing fragrance compositions of the invention with a conventional fragrance composition when the capsules are stored in a Liquid Laundry Product. Samples of fragrance compositions 3, 7 and 11 were encapsulated by the procedure of example 1, along with a conventional fragrance outside the invention. The resulting capsule dispersions were coded Taka21, Taka46, Taka47 and Taka160 respectively. 0.3 g of each capsule dispersion was added to 19.7 g of Persil Kraft Gel Concentrated laundry liquid and after mixing was stored at 40° C. After only 5 hours the sample containing Taka160 was seen to be separating while the remaining samples remained dispersed.

The invention claimed is:

1. A core shell microcapsule which has an average particle size between 1 and 500 micrometers and contains a fragrance composition having a density greater than 0.950 g/cm³ which comprises, prior to encapsulation:
   A) 40 to 85% by weight of at least one cyclic aromachemical material with a density between 0.950 g/cm³ and 1.500 g/cm³ and a ClogP value between 1.00 and 6.00;
   B) 5 to 80% by weight of at least one fragrance material with a density between 0.630 g/cm³ and 0.950 g/cm³; and
   C) 10 to 50% by weight of at least one oil soluble organic compound having a density between 0.950 g/cm³ and 1.500 g/cm³,
   where the sum of A), B) and C) equals 100%,
   wherein the shell is a polymer,
   the cyclic aromachemical material A) is selected from the group consisting of benzyl acetate, benzophenone, benzyl salicylate, cis 3-hexenyl salicylate, coumarin, cyclohexyl salicylate, 3a,4,5,6,7,7a-hexahydro-4,7-methano-1H-inden-5-yl acetate, 3a,4,5,6,7,7a-hexahydro-4,7-methano-1H-inden-6-yl acetate, ethylvanillin, heliotropine, indole, isoeugenol, methyl anthranilate, methyl benzoate, oxane (2-methyl-4-propyl-1,3-oxathiane), 2-phenylethanol, vanillin, vanillin isobutyrate, watermelon ketone, and mixtures thereof, and
   the fragrance material B) is selected from the group consisting of allyl caproate, citronellol, gamma decalactone, dihydromyrcenol, cis-3-hexenyl acetate, limonene, linalool, prenyl acetate, butyl cyclohexyl acetate, and mixtures thereof.

2. The core shell microcapsule according to claim 1, wherein the fragrance composition comprises between 40% and 100% by weight of the cyclic aromachemical material A) with a density between 1.000 g/cm³ and 1.500 g/cm³ and a ClogP value between 1.50 and 5.00.

3. The core shell microcapsule according to claim 1, wherein the fragrance composition comprises between 75% and 100% by weight of the cyclic aromachemical material A) having a ClogP value between 2.00 and 4.50.

4. The core shell microcapsule according to claim 1, wherein the fragrance composition comprises between 5% and 60% by weight of the at least one fragrance material B) with a density between 0.630 g/cm³ and 0.950 g/cm³.

5. The core shell microcapsule according to claim 1, wherein the cyclic aromachemical material A) and fragrance material B) comprise at least 10 kinds of fragrance materials in total.

6. The core shell microcapsule according to claim 1, wherein the oil soluble organic compound C) is selected from the group consisting of acetyl triethyl citrate, diethyl maleate, diethyl malonate, diethyl adipate, dimethyl adipate, diethyl succinate, diethyl tartarate, dimethyl terephthalate, glyceryl triacetate, propylene glycol diacetate, sucrose octa-acetate, sucrose diacetate hexaisobutyrate, glyceryl tripropionate, triethyl citrate, and mixtures thereof.

7. The core shell microcapsule according to claim 1, wherein the fragrance composition further comprises:
   D) 0 to 50% by weight of at least one solvent with a density below 0.950 g/cm³,
   where the sum of A), B), C) and D) equals 100%, and
   where the sum of C) and D) is 50% by weight or less.

8. A liquid consumer product having a density greater than 1.010 g/cm³ and a viscosity between 10 mPas and 5000 mPas measured at either 25° C. or 40° C., which contains the core shell microcapsule as defined in claim 1.

9. The liquid consumer product according to claim 8, having a viscosity between 10 mPas and 2500 mPas measured at either 25° C. or 40° C.

10. The liquid consumer product according to claim 8, which is a household, laundry, personal care or cosmetic composition, and which comprises at least 2% by weight of a surfactant.

11. The liquid consumer product according to claim 10, in which water is the largest component by weight percent.

12. The core shell microcapsule according to claim 1, wherein the at least one cyclic aromachemical material A) has a ClogP value between 2.00 and 6.00.

* * * * *